United States Patent [19]
Liu et al.

[11] Patent Number: 5,401,372
[45] Date of Patent: Mar. 28, 1995

[54] ELECTROCHEMICAL CATALYTIC REDUCTION CELL FOR THE REDUCTION OF $NO_x$ IN AN $O_2$-CONTAINING EXHAUST EMISSION

[75] Inventors: Meilin Liu; Jiemin Zhu; Ashok V. Joshin, all of Salt Lake City, Utah

[73] Assignee: Ceramatec, Inc., Salt Lake City, Utah

[21] Appl. No.: 54,159

[22] Filed: Apr. 26, 1993

[51] Int. Cl.⁶ .............................................. C25B 9/00
[52] U.S. Cl. ................................ 204/295; 204/252; 204/266
[58] Field of Search ................... 204/89 R, 252, 265, 204/266, 295, 290 R, 291, 292, 128, 129, 424, 426, 431

[56] References Cited

U.S. PATENT DOCUMENTS

| | | | |
|---|---|---|---|
| 3,957,949 | 5/1976 | Senjo et al. | 423/235 |
| 3,969,479 | 7/1976 | Lonnes et al. | 423/210 |
| 4,011,298 | 3/1977 | Fukui et al. | 423/235 |
| 4,107,271 | 8/1978 | Atsukawa et al. | 423/235 |
| 4,119,702 | 10/1978 | Azuhata et al. | 423/235 |
| 4,170,550 | 10/1979 | Kamody | 210/23 |
| 4,199,425 | 4/1980 | Sinkevitch | 204/429 |
| 4,253,925 | 3/1981 | Mason | 204/129 |
| 4,478,798 | 10/1984 | Karwat | 423/224 |
| 4,640,825 | 2/1987 | Rosenberg | 423/235 |
| 4,664,903 | 5/1987 | Becker et al. | 423/573 R |
| 4,780,277 | 10/1988 | Tanaka et al. | 422/4 |
| 4,789,530 | 12/1988 | Johnson et al. | 423/226 |
| 4,844,874 | 7/1989 | deVries | 423/210 |
| 4,908,194 | 3/1990 | Hooper | 423/235 |
| 4,980,040 | 12/1990 | Lichtin et al. | 204/157.46 |
| 4,999,998 | 3/1991 | Akerib | 60/274 |
| 5,034,112 | 7/1991 | Murase et al. | 204/425 |
| 5,149,512 | 9/1992 | Li et al. | 423/239 |
| 5,171,553 | 12/1992 | Li et al. | 423/239 |

OTHER PUBLICATIONS

Armor, John N., "Environmental Catalysis," Applied Catalysis B: Environmental, 1, pp. 221–256, 1992.

Bosch et al., "Catalytic Reduction of Nitrogen Oxides, A Review of the Fundamentals and Technology," Catalysis Today, vol. 2, No. 4, pp. 369–521, Apr., 1987.

Gur et al., "Decomposition of Nitric Oxide Using Solid State Electrolyte," pp. 109–112, 1979.

Haber et al., "The Structure and Redox Properties of Vanadium Oxide Surface Compounds," Journal of Catalysis, 102, pp. 52–63, 1986.

Heinemann et al., "Improved Industrial Catalysts," Lawrence Berkeley Laboratory, University of California, Materials & Chemical Sciences Division, pp. 1–89, Feb., 1989.

Janssen et al., "Mechanism of the Reaction of Nitric Oxide, Ammonia, and Oxygen over Vanadia Catalysts," The Journal of Physical Chemistry, vol. 91, No. 23, pp. 5921–5927, 1987.

Mizumoto et al., "Effects of Coexisting Gases on the Catalytic Reduction of NO with $NH_3$ over Cu(II) NaY," Journal of Catalysis, 59, pp. 319–324, 1979.

Nam et al., "Model of Temperature Dependence of a Vanadia-Alumina Catalyst for NO Reduction by $NH_3$: Fresh Catalyst," Ind. Eng. Chem. Prod. Dev. 25(2), pp. 186–192, 1986.

Otto et al., "Studies of Surface Reactions of Nitric Oxide by Isotope Labeling," The Journal of Physical Chemistry, vol. 76, No. 1, pp. 37–43, 1972.

(List continued on next page.)

*Primary Examiner*—Kathryn Gorgos
*Attorney, Agent, or Firm*—Trask, Britt & Rossa

[57] ABSTRACT

Disclosed are a process and apparatus for removing $NO_x$ in an $O_2$-containing exhaust emission based on electrochemically catalytic reduction processes. Advantages to the electrochemically catalytic reduction process include high $NO_x$ conversion efficiency and suitability for the removal of $NO_x$ from the $O_2$-containing exhaust of mobile combustion sources due to the simplicity in construction, maintenance and operation (chemical-reducing agents are not required in the process).

13 Claims, 3 Drawing Sheets

OTHER PUBLICATIONS

Otto et al., "Studies of Surface Reactions of Nitric Oxide by Nitrogen-15 Isotope Labeling," The Journal of Physical Chemistry, vol. 74, No. 13, pp. 2690–2698, 1970.

Pancharatnam et al., "Catalytic Decomposition of Nitric Oxide on Zirconia by Electrolytic Removal of Oxygen," J. Electrochem. Soc., 122, 869, pp. 14–20, 1975.

Wakihara et al., "Decomposition of NO Using Chevrel Phase Sulfides," Abstract, #X27.

Wong et al., "Reduction of NO with $NH_3$ on $Al_2O_3$- and $TiO_2$-Supported Metal Oxide Catalysts," Ind. Eng. Chem. Prod. Res. Dev., vol. 25, No. 2, pp. 179–186, 1986.

Air Products and Chemicals, Inc., Air Products Company Overview.

Li et al., "Catalytic decomposition of nitrous oxide on metal exchanged zeolites", Applied Catalysis Environmental, 1, pp. L21–L29, 1992.

Li et al., "Catalytic Reduction of Nitrogen Oxides With Methane in the Presence of Excess Oxygen", vol. 1, No. 4 (1992) L31.

Szalkowski et al., "Auger Electron Spectroscopy Investigations of the Surface Chemical Composition of Vanadium, the Vanadium Oxides, and Oxidized Vanadium", J. Chem. Phys., 56, 12, pp. 6097–6103, 1972.

ELECTROCHEMICAL CATALYTIC REDUCTION CELL FOR THE REDUCTION OF $NO_x$ IN AN $O_2$-CONTAINING EXHAUST EMISSION

TECHNICAL FIELD

The invention relates to a method and apparatus for reducing $NO_x$ in exhaust emissions.

BACKGROUND

Although nitric oxides are thermodynamically unstable relative to their molecular elements, it is kinetically difficult to decompose the compounds. Thus, the removal of the toxic and polluting nitrogen oxides ("$NO_x$") from emission of combustion sources, nitric plants, or other chemical processes, has been investigated under various conditions, including thermal, chemical, photo, and electrochemical reduction in the presence of catalysts. To date, numerous chemical reducing agents (e.g., CO, $NH_3$, $H_2$, $CH_4$, etc.) and catalysts (e.g., noble metals, pure and mixed metal oxides) have been introduced to enhance the kinetics of $NO_x$ decomposition.

Chemical processes based on catalysts and chemical-reducing agents have seen commercial applications in large-scale removal of $NO_x$ from stationary combustion sources and nitric plants. However, the efficient removal of this pollutant from mobile combustion sources remains an environmental problem. One purpose of this invention is to explore avenues through which the $NO_x$ emitted from $O_2$-containing gas-fired engines can be successfully removed without introducing chemical-reducing agents.

In the late seventies and early eighties, the electrochemical reduction of $NO_x$ was actively pursued. Most of the work concentrated on blackened zirconia electrolyte with noble metal electrode. A problem with such an approach is the low conversion level due to the fact that the noble metals (such as platinum and gold) not only adsorb $NO_x$, but also actively adsorb other reducible gas species, particularly oxygen, in the exhaust gas stream.

A successful chemical technique to remove $NO_x$ in oxygen-containing environments is the so-called Selective Catalytic Reduction (SCR) of $NO_x$ with $NH_3$:

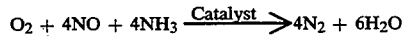

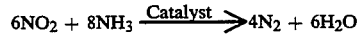

Supported vanadium oxide ($V_2O_5$) is one of the best catalysts for SCR because of its high resistance to poisoning by sulphur oxides. It has been shown that the catalytic reactions are essentially a redox reaction of 5 valent and 4 valent vanadium.

For the removal of $NO_x$ from emissions of mobile combustion sources (such as diesel engines), however, the injection of a chemical-reducing agent is very inconvenient and an alternative process which selectively reduces $NO_x$ and requires no chemical-reducing agent would be an improvement in the art.

DISCLOSURE OF THE INVENTION

The invention includes an electrochemical process for separating $NO_x$ from a $O_2$-containing gas stream and converting the separated $NO_x$ to elemental nitrogen and oxygen, without using chemical-reducing agents and using minimal energy consumption. To accomplish this, an electrochemical cell is provided having catalytically-active electrodes and a solid oxide electrolyte. The $NO_x$-containing gas stream is brought into contact with a cathode and reduced to nitrogen and oxygen ions. The oxygen ions migrate to an anode where they are oxidized to form elemental oxygen.

The invention is useful for, among other things, the removal of $NO_x$ from the flue gases of a combustion process, whether the process is associated with the combustion of diesel, gasoline, LPG, coal, or other hydrocarbon fuel.

BRIEF DESCRIPTION OF THE FIGURES

In the drawings, which depict presently preferred embodiments of the invention and in which like reference numerals refer to like parts in different views.

BEST MODE OF THE INVENTION

Figure 1:
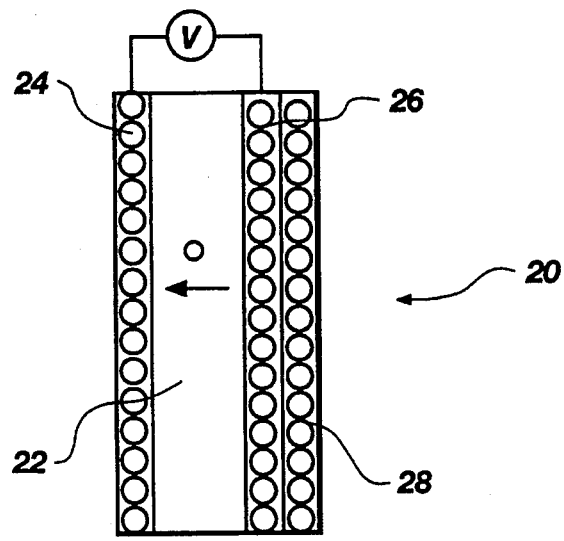
FIG. 1 is a schematic representation of an electrochemical cell for $NO_x$ reduction in an oxygen-containing exhaust emission.

As shown in FIG. 1, an electrochemical cell for $NO_x$ removal, generally 20, includes a solid oxide electrolyte 22 with a porous anode 24 and porous cathode 26 at opposite sides of the electrolyte 22. The electrolyte 22 preferably comprises an 8 mole percent yttria stabilized zirconia membrane 0.02 inch (0.5 mm) thick. The cathode 26 is a highly porous, gas-diffusion catalyst, such as supported vanadia oxides and other transition metal oxides. Abutting the cathode is an electron collecting layer 28 (e.g. a conductive perovskite-type oxide) which enhances the electrical conductivity of the resistive cathode 26. A highly porous, gas-diffusion electrode or anode 24 contacts the electrolyte membrane 22 on the other side. The anode 24 is preferably silver or another metal which is electrically conductive and chemically stable under the operating conditions.

Figure 2:
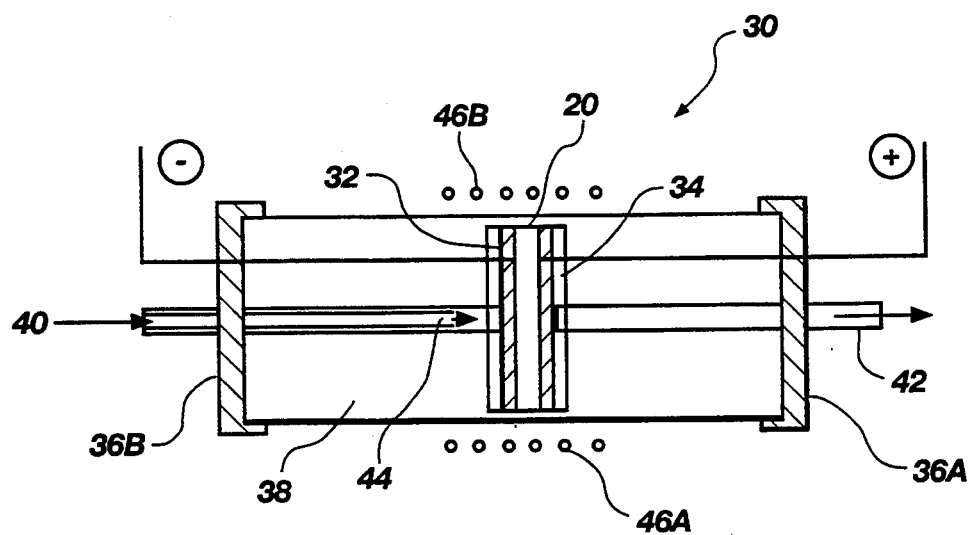
FIG. 2 depicts schematically an $NO_x$ removal device utilizing the electrochemical cell of FIG. 1.

As shown in FIG. 2, an electrochemical cell is incorporated into an $NO_x$ removal device, generally 30. The electrochemical cell 20 is preferably supported by a porous metal grid 32 contained within a grid supporter 34. The electrochemical cell 20, porous metal grid 32, and grid supporter 34 are contained within an air-tight reactor 36A, 36B forming a reaction chamber 38.

Gas feeds into the reaction chamber 38 through gas inlet 40. Reacted gas leaves the reaction chamber 38 via gas outlet 42. Inside the gas inlet is a thermocouple 44. Heating elements 46A, 46B are preferably placed outside of the reaction chamber 38 proximate the electrochemical cell 20. Electrical power is supplied to the porous metal grid 32 either from a battery, generator, alternator or other source.

The electrodes 24, 26 of the electrochemical wall 20 are catalytically-active. A $NO_x$-containing gas stream is fed in through the gas inlet 40 where it contacts the cathode 26 and is reduced to nitrogen and oxygen ions. The oxygen ions migrate to the anode 24 where they are oxidized to form elemental oxygen.

Two porous metal grids 32 held by two ceramic supporters 34 contact the electron collector layer 28 in cathode side and metal layer in anode side, respectively (FIG. 2).

In operation, a gas stream containing $NO_x$ is directed through inlet port 40 into the first region where it contacts the cathode 26. Voltage is applied through the metal grids from an external power source. The metal grids are preferably welded with two silver wires, and between the cathode 26 and anode 24.

The $NO_x$ diffuses into the gas/cathode/electrolyte three-phase region and, under the applied voltage, it is believed to react (with the use of the vanadium pentaoxide catalyst) according to the following reactions:

At the same time, $O^=$ is migrating to the anode 24 and leaves oxygen vacancies behind. Accordingly, the surface of $V_2O_5$ is full of oxygen vacancies and $V^{+4}$ sites, which are very active for absorption and chemical reduction of $NO_x$. Thus, the following reaction is believed to proceed:

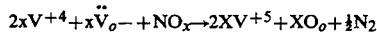

That is, the adsorbed $NO_x$ is believed to re-oxidize the reduced $V^{+4}$ back to the original oxidation state.

The oxygen ions then migrate across the electrolyte membrane 22 and then are oxidized to elemental oxygen as follows:

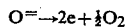

The overall reaction is

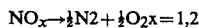

For large scale removal of $NO_x$ from a gas stream, a stack of the inventive electrochemical cells could be utilized.

The invention is not limited to use of the previously identified supported vanadium pentaoxide ($V_2O_5$) oxides as the cathode. Any oxide with the following properties should be a suitable catalyst for this process:

(1) The oxide constitutes a redox couple, i.e., the oxide can be relatively easily reduced and, in turn, the reduced form can be easily re-oxidized back to the original oxidation state.

(2) During reduction of the oxide, oxygen vacancies are simultaneously created and the reduced sites selectively adsorb $NO_x$.

In many cases, metal oxides in the reduced form absorb $NO_x$ faster and stronger, as for instance on $Cu^{+1}$ ions versus $Cu^{+2}$, $Cr^{+2}$ ions vs. $Cr^{+3}$, $Fe^{+2}$ vs. $Fe^{+3}$, and $Mn^{+2}$ vs. $Mn^{+4}$.

Typical porous catalysts for use with the invention include: $(V_2O_5)_x(TiO_2)_{1-x}$, $(V_2O_5)_x(SiO_2)_{1-x}$, $(V_2O_5)_x(\gamma-Al_2O_2)_{1-x}$, $CuO_2$, $SnO_2$, $NiO$, $Fe_3O_4$, $Nb_2O_5$, LCF (i.e. $LaCu_{1-x}Fe_xO_3$), $[(Bi_2O_3)_{1-x}(Y_2O_3)_x]_{1-k}(LSCF)_k$, (i.e.,$[(Bi_2O_3)_{1-x}(Y_2O_3)_x]_{1-k}(La_{1-y}Sr_yCo_{1-x}Fe_xO_3)_k$), LSMCF (i.e. $La_{1-x}Sr_xMn_{1-y-z}Cu_yFe_xO_3$), $Cu_xMo_6S_8$, and mixtures thereof.

Similarly, the invention is not limited to use of the above-mentioned $Y_2O_3$-stabilized zirconia as the electrolyte. Numerous stabilized oxygen ion-conductive oxides may be employed as the solid electrolyte. These include, but are not limited to:

(1) Ceria-based, e.g., $(CeO_2)_{1-x}(CaO)_x$, $0.09 < x < 0.15$;
(2) Zirconia-based, e.g., $(ZrO_2)_{1-x}(Yb_2O_3)_x$, $0.07 < x < 0.12$; and
(3) Bismuthia-based, e.g., $(Bi_2O_2)_{1-x}(Er_2O_3)_x$, $0.09 < x < 0.15$.

Dye to the high resistivity of the catalyst 26, a conductive layer is preferably employed on the top of the catalyst to enhance the overall conductivity of the electrochemical cell meanwhile maintaining the selective absorption of $NO_x$ when other reducible gas species, particularly $O_2$, are present in the gas stream.

In electrochemical process, noble metals such as platinum are generally used as electron collectors or electrodes. However, the catalytic reduction of $NO_x$ on platinum group metals is markedly inhibited by $O_2$ in gas stream. This behavior has been attributed to preferential chemisorption of $O_2$ over $NO_x$ on the platinum surface.

In the present invention, perovskites, e.g., lanthanum strontium manganate ("LSM" i.e. $La_{1-x}Sr_xMnO_{3-y}$, $x = 0.01 - 0.99$), which are chemically and thermally compatible with the catalyst 26 and the electrolyte membrane 22, may be employed. Considerable $NO_x$ reduction (30%) has been achieved by this cell configuration at acceptable energy consumption levels.

Typical electron collecting layers are made from a material selected from the group consisting of LSM, LSMC (i.e. $La_{1-x}Sr_xMn_{1-y}Co_yCo_yO_3$), LSC (i.e. $La_{1-x}Sr_xCoO_3$), LSCF (i.e. $La_{1-x}Sr_xCo_{1-y}Fe_yO_3$), platinum and mixtures thereof.

The unique advantages offered by these approaches include:

(1) A decreased sensitivity to any $O_2$ present due to the unique electrochemical call design. This advantage can be extremely important in applications such as for treating the exhaust of a diesel engine wherein 10 to 15% of the exhaust maybe oxygen.

(2) A chemical-reducing agent is not involved and hence the invention is highly desirable for mobile and small scale combustion sources. For example, no ammonia is present to be released with the exhaust gas (i.e. there is no "slip").

(3) A high $NO_x$ conversion is achieved with less energy consumption due to the electrochemically-enhanced catalytic activity of the catalysts. Furthermore no toxic $N_2O$ is formed.

(4) A device utilizing the technology is compact and portable. Analysis indicates that the device can be relatively small in size. Such a small size allows for both stationary and mobile applications. For especially stationary applications, the device can be used in combination with other technologies, e.g. SCR as sequential filters.

(5) As demonstrated in the EXAMPLES, the cell operates at relatively low voltages, allowing typical mobile power source (e.g. a generator/alternator or battery) to be used.

(6) For internal combustion applications, the presence of lead in the gas stream will not poison the electrochemical cell.

The invention is further described by the following illustrative examples.

EXAMPLE I

A device such as that depicted in FIGS. 1 and 2 was made. The cell structure consisted of a 0.02" thickness of hereinafter described materials for the solid oxide electrolyte, porous silver was used as the anode, vanadia pentaoxide was used as the porous cathode, LSM was used as the electron collecting layer, while platinum served as the porous metal grid.

1. Preparation of Electrolyte Materials

Three types of oxygen conductive solid electrolytes were prepared: (1) fully-stabilized cubic $(ZrO_2)92\%(Y_2O_3)8\%$, (2) full-stabilized cubic $(ZrO_2)91\%(Y_2O_3)4.5\%(Yb_2O_3)4.5\%$ and (3) $(CeO_2)85\%(CaO)15\%$.

2. Catalyst Preparation

2.1. Impregnation

Supported vanadia based catalysts were prepared by impregnation which is a procedure whereby a certain volume of solution containing a compound of vanadium is totally adsorbed into the pores of a support. Supports are used to improve mechanical strength, thermal stability, lifetime, as well as selectivity and activity. Commercially available $TiO_2$(Degussa P25) and y-$Al_2O_3$ (Degussa) supports were used.

The support materials were first wetted with high purity distilled water and dried overnight in the 50° to 120° C. temperature range. The desired amount of $NH_4VO_3$ was added to 1 to 10M oxalic acid solution, which on heating formed $(NH_4)_2[VO(C_2O_4)_2]$ complex. The solution was added to the support, and the water removed by evaporation with continuous stirring. The resulting solid was dried overnight at 50° to 120° C. and was calcined in flowing air for a few hours in the 400° to 600° C. temperature range. Designed vanadium contents were configured by Inductively Coupled Plasma Spectroscopy and X-ray diffraction. Surface areas were measured by BET method.

2.2. Solution Precipitation

The catalyst was also synthesized by solution precipitation techniques.

Ammonium vanadate ($NH_4VO_3$) was reacted with titanium tetrachloride ($TiCl_4$) in aqueous solution to form titanium vanadate precipitates. At the same time, titanium tetrachloride reacted with ammonium hydroxide ($NH_4OH$) in aqueous solution to form titanium hydroxide precipitates. After filtration and drying, the two precipitates (titanium vanadate and titanium hydroxide) were mixed with appropriate proportions and were calcined in a temperature range of 400° to 600° C. for a few hours. The resulting powders were confirmed by Inductively Coupled Plasma Spectroscopy and X-ray diffraction.

3. Processing of Porous Cathode

Open porous catalysts were prepared as described as following:

(1) The prepared catalysts were finely divided into small particles by ball milling;

(2) The finely-divided particles, after drying, were then mixed with an appropriate organic binder in a suitable solvent to make a paste;

(3) The paste was screen printed on one side on the electrolyte; and (4) The paste was dried at 50° C. and fired in a temperature range between 400° to 500° C. to burn off the organics and form an open porous catalyst.

4. Processing of Perovskites Conductive Layer

Due to the high resistivity of the vanadia-based catalyst, a conductive layer is preferably employed on the top of the catalyst to enhance the overall conductivity of the electrochemical cell meanwhile maintaining the selective absorption of $NO_x$ when other reducible gas species, particularly $O_2$, are present on the gas stream.

The Perovskites conductive materials, e.g., strontium doped lanthanum manganate (LSM), were synthesized by a gel resin process. In this process, soluble salts of the chemical constituents such as La, Mn, and Sr were dissolved in water. Citric acid and ethylene glycol were than added to this solution. An appropriate amount of citric acid was chosen so that four ligands were available to which the metal ions can attach. Ethylene glycol polymerized the citric acid by a slow and controlled drying process. The result amorphous mixture was then calcined to yield oxides which were than reactively calcined in air to give a homogeneously doped powder. The powder was then milled and sieved to achieve a uniform particle size. The phases of the powder was examined by X-ray diffraction.

5. Cell Fabrication

Flat-plate electrochemical cells were designed and fabricated for simplicity on construction and operation as well as accuracy in evaluation of the critical parameters. Fully-stabilized cubic zirconia electrolytes were used in this study.

The cathode of the cell was titania supported vanadia catalyst, which was applied on one side of the electrolyte disk. The Perovskite conductive layer was coated on the top of the vanadia layer. The anode of the cell was silver. All the coatings were screen-printed. The thickness of screen-printed Ag, $V_2O_5$ and Perovskites coatings is approximately 20 microns.

To improve the adherence of the catalyst film on tape-casted $ZrO_2$ pellets, the pellet surfaces were roughen by adding a slurry containing fine (1-2 $\mu m$) $ZrO_2$ powder, followed by drying and firing at 1500° C.

Both cathode and anode were mechanically bonded with two platinum grids, which were connected to two silver wires, acting as electrical leads.

6. Characterization of Electrochemical Cells

Four-point and two-point impedance spectroscopy was extensively used to characterize the electrical properties of impedance response of each individual component of the cells, such as electrolyte, electrode, and catalyst, as well as the electrochemical systems. The phase composition of various materials were investigated using X-ray diffraction.

Fabricated cells were examined by potential sweep techniques to ensure that the cells made were functioning electrochemically. In case of high internal resistance, the cell was diagnosed by impedance spectroscopy to resolve the electrolyte resistance from the interfacial resistance, identifying the source of high impedance.

7. Analysis of Gases

The catalytic tests of $NO_x$ reduction of the electrochemical cell was carried out in the experimental apparatus sketched in FIG. 2. Three gas lines carrying $NO_x/N_2$, $O_2$ and $N_2$ respectively, allow for adjustments in the concentrations and flow rate of $NO_x$, $O_2$ and $N_2$. The reaction temperature, measured by a chromel-alumel thermocouple, was controlled in the range between 300° to 500° C. The $NO_x$ and $O_2$ concentrations were measured by a HP 5890 chromatography equipped with a Haysep "D" 30' packed column, and a UTI Quadrupole Mass Spectrometer before and after the voltage was applied. A commercially available NO sensor (EIT) and $O_2$ sensor (Ceramatec) was also connected in the gas line to confirm the $NO_x$ and $O_2$ concentration. Applied voltage was supplied from a constant potential source ranging from 0 to 5 volts. The $NO_x$ conversion efficiency was calculated based on the $NO_x$ concentration changes before and after the voltage was applied.

Figure 3:
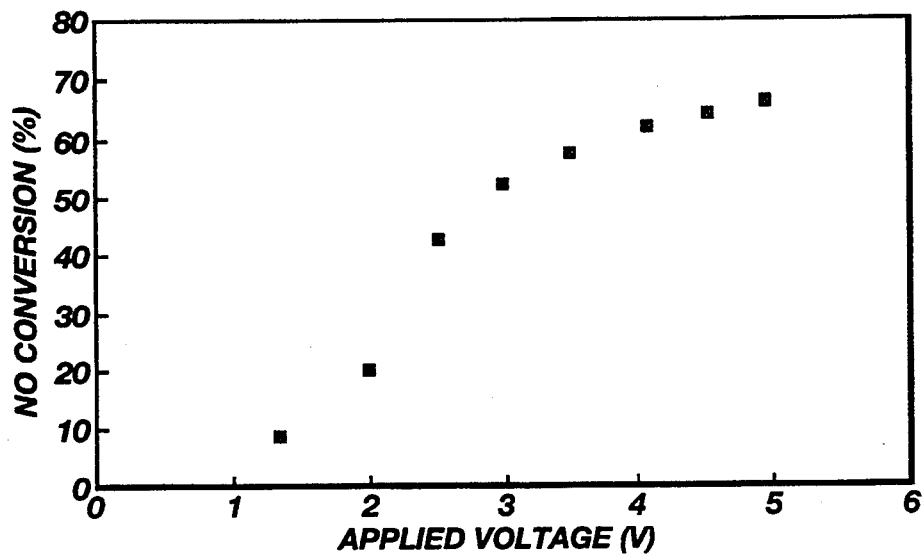
FIG. 3 is a graph showing the corresponding power consumption (BHH/g) of the $NO_x$-reducing activity of the electrochemical cell identified in FIG. 1 and used in a device identified in FIG. 2 at varied voltage with a low $O_2$ concentration gas stream.

8. Effect of Increasing Voltage when Gas Contained Low Concentration of $O_2$ Fifty cc per minute of a gas was passed through the gas inlet of the device at a temperature of 350° C. The gas contained 600 ppm NO and 2000 ppm oxygen. A DC voltage was applied across the electrochemical cell and was steadily increased from 0 to 5 volts. The amount of NO conversion at each voltage is displayed graphically in FIG. 3. It shows that the reduction of $NO_x$ is an electrochemically activated process, as indicated by the shape of the conversion curve as a function of the applied voltage. When the applied voltage is lower than the theoretical reduction potential of $V+5$ to $V+4$, the conversion efficiency is negligible. As the applied voltage exceeds the theoretical reduction potential of $V+5$, the conversion efficiency rapidly increases with the increase of the applied voltage up to the point, where the applied voltage is sufficiently high to reduce all available $NO_x$. Thereafter, the conversion efficiency becomes relatively independent of the applied voltage.

Figure 4:
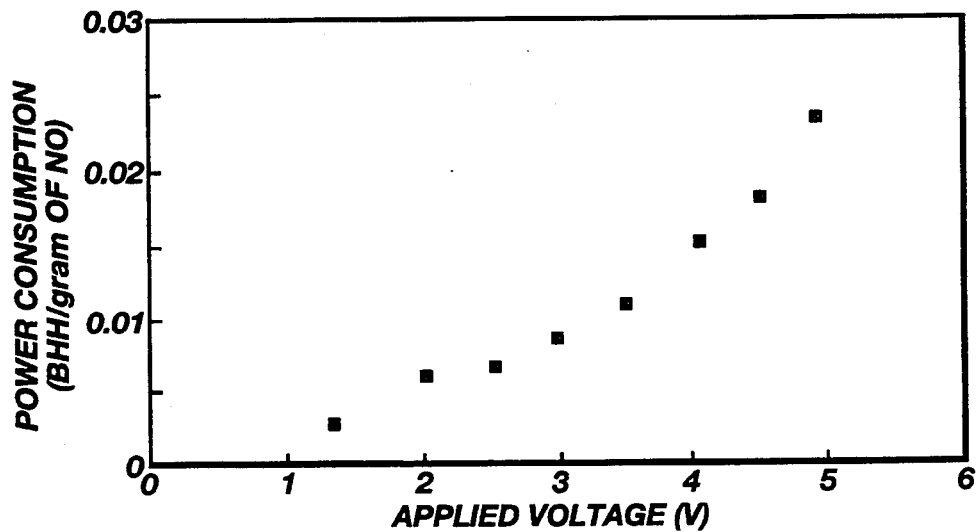
FIG. 4 is a graph showing the corresponding power consumption (HH/g) of the device for $NO_x$-reduction at varied applied voltages under low $O_2$ concentration.

9. Power Consumption at Various Voltages when Gas Contained Low Concentration of $O_2$ The power consumption in brake horsepower-hours per gram of $NO_x$ for the experiment of EXAMPLE 1.8 was measured. The Results are graphically depicted in FIG. 4. As can be deduced from FIGS. 3 and 4, from an efficient power consumption point of view, the system is preferably operated at a voltage of less than 3 volts DC.

Figure 5:
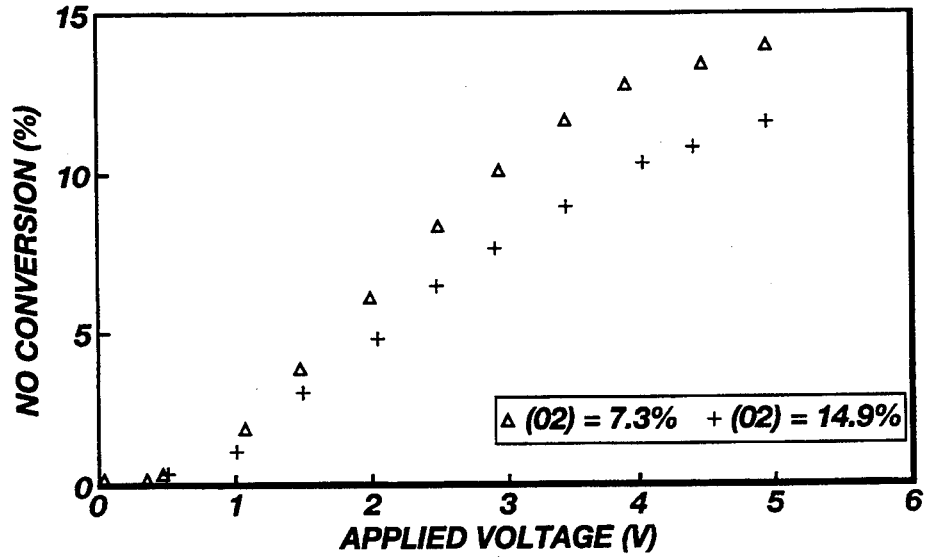
FIG. 5 is a graph depicting the percentage of $NO_x$ converted with varying applied voltages of a device built according to the invention.

10. Effect of Increasing Voltage when Gas Contained High Concentration Of $O_2$ The experiment of EXAMPLE 1.8. was repeated at various oxygen concentrations. FIG. 5 represents $NO_x$ conversion efficiency under 7 and 15% oxygen containing gases. The $NO_x$ conversion efficiency increases with the increase of the applied voltage above 0.5 volts. The figure also indicates that oxygen is a strong competing species during the $NO_x$ region process.

11. Power Consumption as a Function of $O_2$ Concentration

Figure 6:
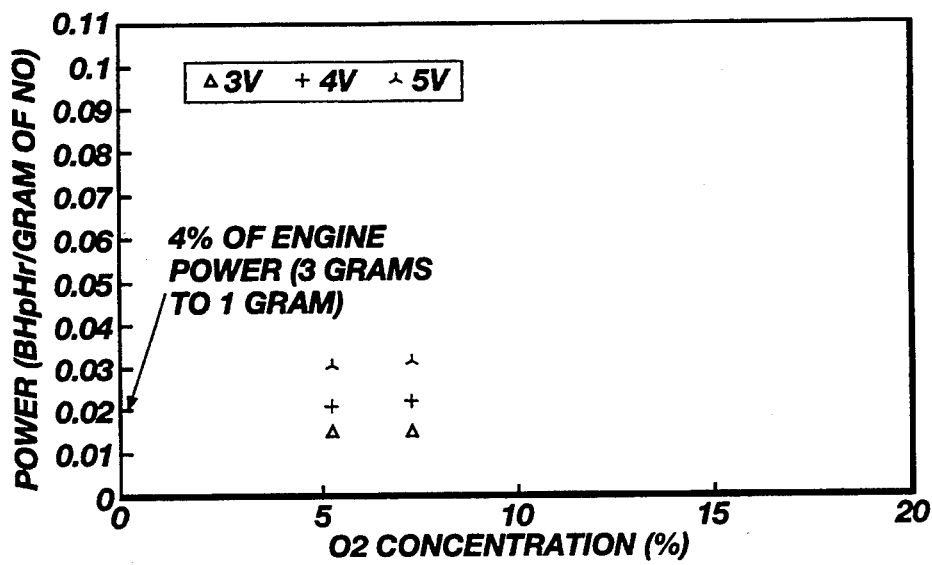
FIG. 6 is a graph showing the power used per gram of NO at various applied voltages and at varying oxygen concentrations.
Figure 7:
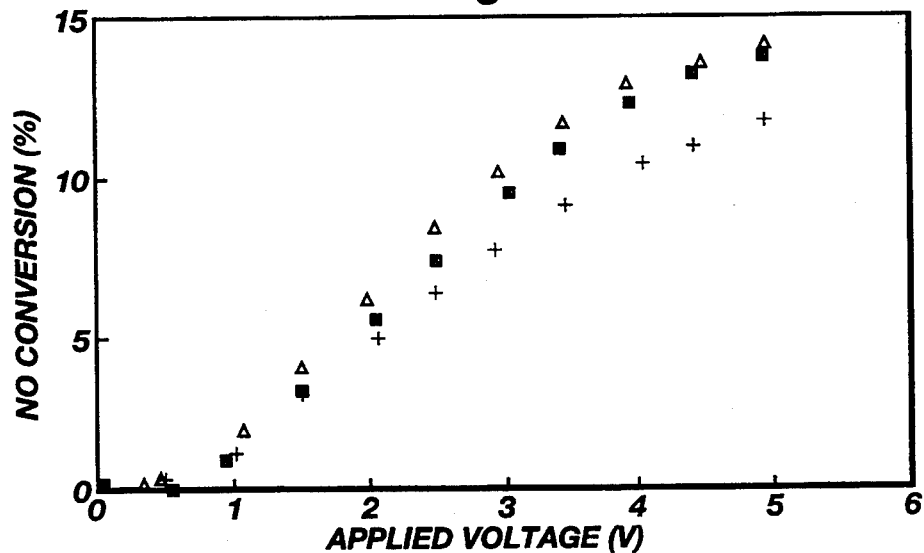
FIG. 7 is a graph depicting the percentage of $NO_x$ converted with varying applied voltages of a device built according to the invention at varied oxygen concentrations.

FIG. 6 shows the power consumption of the electrochemical cell at various $O_2$ concentrations under three applied voltages. The arrow on the graph indicates that 0.02 BHpHr/gram of $NO_x$ is equivalent to 4% of total engine power of a 400 horse-power engine.

12. Effect of Gas Temperatures

Thirty cc per minute of a gas was passed through the gas inlet of the device. The gas contained 550 ppm NO; 6.2% oxygen, with a balance of nitrogen at a constant DC voltage of 2 volts applied across the electrolyte.

The temperature was increased from 350° to 430° C. while the percentage NO conversion was measured. The amount of NO conversion at varying gas temperatures is displayed graphically in FIG. 8.

Figure 8:
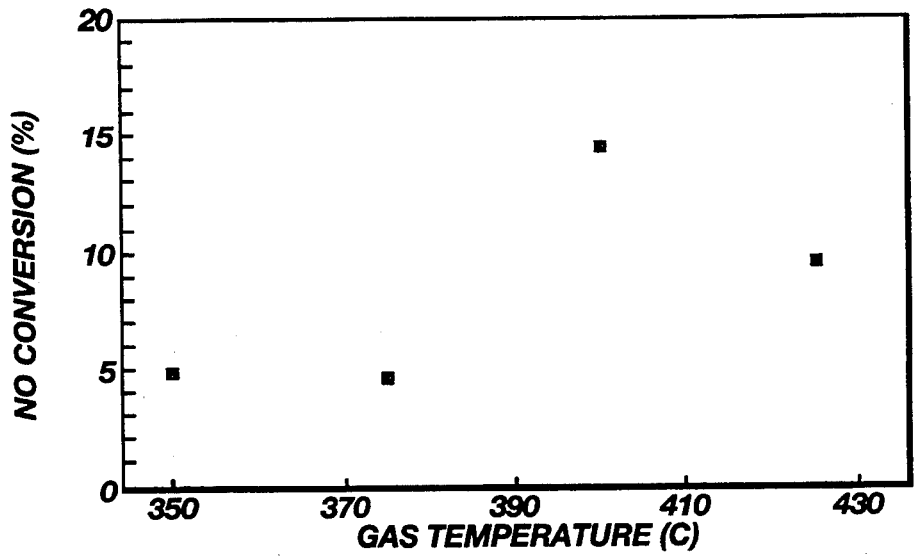
FIG. 8 is a graph showing the $NO_x$ conversion performance of the device at various gas temperatures.

As demonstrated by FIG. 8, operation of this particular system at temperature higher than about 400° C. is not advisable evidently due to the considerable portion of the energy being consumed in the transport of oxygen through the electrolyte at such high temperature.

EXAMPLE II

Based on the data available, the approximate size of the devices for diesel engines was estimated as follows:

Condition: Exhaust flow from diesel engines is 12 lb./min. with 280 ppm NO, 14 ppm $NO_2$, and 28 ppm $SO_2$ Case I: 100% Electrochemical Reduction In this case, it is assumed that (i) no chemical decomposition of $NO_x$ and $SO_x$ occurs, i.e., the oxides of nitrogen and sulfur are electrochemically decomposed and hence all the oxygen ions are pumped through the electrolyte, and (ii) there is no electrochemical reduction of other reducible species ($O_2$, $H_2O$, CO) due to the selective adsorption of $NO_x$ on $TiO_2$/$V_2O_5$ catalysts.

The oxygen-ion molar flux can be expressed as $$N_{o-} = \left(\frac{12 \text{ lb.}}{\text{min}}\right)\left(\frac{454 \text{ g}}{\text{lb.}}\right)\left(\frac{(1)(2.8 \times 10^{-4})}{(30)} + \frac{(2)(1.4 \times 10^{-5})}{(46)} + \frac{(2)(2.8 \times 10^{-5})}{(64)}\right) =$$

$$589.31 \times 10^{-4} \text{ mol./min.} - 9.822 \times 10^{-4} \text{ mol./sec.}$$

The current required can be expressed as $$I = 189.53(A)$$

Assuming that the operating current density is 200 $mA/cm^2$, which has been demonstrated for over 3000 hours for other oxygen-ion related devices, the surface area required to deliver 189.53 A current is 947.65 $cm^2$ or 1.02 $ft.^2$. This can be easily achieved by stacking 40 flat-plate electrochemical cells, each having a surface area of 25 $cm^2$ (2"×2"). The multilayer-stacking technology is established for fuel cells. Thus, the device will preferably have dimensions of 2½"×2½"×8" (6.4 cm×6.4 cm×20.3 cm).

Case II: 100% Chemical Reduction In this case, it is assumed that all of the $NO_x$ and $SO_x$ is chemically decomposed at the catalysts and there is no electrochemical reduction of $NO_x$ and hence there is no required current at all. Thus, the cathodes can be made in open porous form with effective surface area of several m2/gram and the functional unit of the system is potentially small in size.

In reality, however, the electrochemical reduction and the electrochemically-induced chemical reaction will occur simultaneously. Thus, the actual current and hence the surface a area required for the removal of $NO_x$ will be much smaller than the numbers estimated in Case I. Accordingly, in theory, the dimension of a device should be somewhere between the sizes estimated in Case I and Case II.

EXAMPLE III

Estimation of Power Consumption

Condition: $No_x$ discharge rate from diesel engines is 4.5 g/hp-hr;

Assumption: 100% electrochemical reduction, i.e., all oxygen anions decomposed from $NO_x$ will be pumped through the electrolyte and there is no chemical decomposition.

Estimation:

$$\frac{4.5)}{(30)} (2)(96,485)(Coulombs)/2,684,520(watts\text{-}sec) =$$

0.01078 (Coulomb/Watt-sec)

| Applied Voltage (V) | Power Consumption (%) | | |
|---|---|---|---|
| | 100% Removal | 80% Removal | 65% Removal |
| 1 | 1.08 | 0.86 | 0.70 |
| 0.9 | 0.97 | 0.78 | 0.63 |
| 0.8 | 0.86 | 0.69 | 0.56 |
| 0.7 | 0.75 | 0.60 | 0.49 |
| 0.6 | 0.65 | 0.52 | 0.42 |
| 0.5 | 0.54 | 0.43 | 0.35 |
| 0.4 | 0.43 | 0.34 | 0.28 |
| 0.3 | 0.32 | 0.26 | 0.21 |

For the electrochemically-catalyzed chemical reduction process, however, there is virtually no power consumption in the ideal case. Therefore, the power consumption should range from 0 to about 1% of power output. depending on how much of the $NO_x$ or $SO_x$ is decomposed chemically rather than electrochemically. For 65% removal of $NO_x$ and $SO_x$, the power consumption should be less than 0.7% of the power output.

Although the invention has been described with regard to certain preferred embodiments, the scope of the invention is to be defined by the appended claims.

What is claimed is:

1. An electrochemical cell for reduction of NOx comprising:
   (a) a solid electrolyte having sides;
   (b) an anode on one side of the solid electrolyte;
   (c) two layers on the side of the solid electrolyte opposite that of the anode, one of said layers is a porous oxide catalyst, and the other layer is an electron conducting layer, said electron conducting layer made from a material selected from the group consisting of lanthanum strontium manganate, lanthanum strontium manganese cobalt oxide, lanthanum strontium cobalt oxide, lanthanum strontium cobalt ferride, platinum and mixtures thereof; and
   (d) a circuit that applies a potential across said anode and either said porous oxide catalyst or said electron conducting layer.

2. The electrochemical cell of claim 1 wherein said electron conducting layer is sandwiched between the solid electrolyte and the porous catalyst, and serves as a cathode.

3. The electrochemical cell of claim 1 wherein said porous catalyst is sandwiched between the solid electrolyte and the electron conducting layer, and serves as a cathode.

4. The electrochemical cell of claim 1 wherein said porous oxide catalyst is made from a material selected from the group consisting of $(V_2O_5)_x(TiO_2)_{1-x}$, $(V_2O_5)_x(SiO_2)_{1-x}$, $(V_2O_5)_x(\gamma\text{-}Al_2O_3)_{1-x}$, $CuO_2$, $SnO_2$, $NiO$, $Fe_3O_4$, $Nb_2O_5$, lanthanum copper ferride, lanthanum strontium manganese copper ferride, $Cu_xMo_6S_8$, and mixtures thereof, wherein x is 0.01 to 0.99.

5. An electrochemical cell for nitrogen oxide reduction comprising:
   a solid electrolyte having sides;
   a metallic anode positioned on one side of said solid electrolyte;
   a cathode positioned on the side of the solid electrolyte opposite that of the metallic anode, said cathode comprising a porous gas-diffusion catalyst; and
   a conductive layer, comprising a perovskite oxide, positioned on the cathode to enhance the conductivity of the electrochemical cell and maintain the selective absorption of nitrogen oxide.

6. The electrochemical cell of claim 5 wherein said solid electrolyte is selected from the group consisting of an yttria-stabilized zirconia, stabilized zirconia, stabilized bismuthia, stabilized ceria, and mixtures thereof.

7. The electrochemical cell of claim 5 wherein said cathode is nonstoichiometric $V_2O_5$.

8. The electrochemical cell of claim 5 wherein said anode is silver.

9. The electrochemical cell of claim 5 wherein said conductive layer comprises lanthanum strontium manganate.

10. A device for the electrochemical reduction of $NO_x$ comprising:
    (a) a container;
    (b) an electrochemical cell, contained within said container, said electrochemical cell comprising:
       (i) a solid electrolyte having sides,
       (ii) a metallic anode positioned on one side of said solid electrolyte,
       (iii) a cathode positioned on the side of the solid electrolyte opposite that of the metallic anode, said cathode comprising a porous gas-diffusion catalyst, and
       (iv) a conductive layer positioned on the catalyst to enhance the conductivity of the electrochemical cell and maintain the selective absorption of nitrogen oxide;
    (c) a gas inlet leading into said container, said gas inlet directed to the electrochemical cell;
    (d) a porous metal grid surrounding said electrochemical cell;
    (e) a power source for electrifying said porous metal grid and said cathode; and
    (f) a gas outlet for removing gas from said container.

11. An electrochemical cell for reduction of NOx comprising:

(a) a solid electrolyte having sides;
(b) an anode on one side of the solid electrolyte;
(c) two layers on the side of the solid electrolyte opposite that of the anode, one of said layers is a porous oxide catalyst, said porous oxide catalyst made from a material selected from the group consisting of $(V_2O_5)_x(TiO_2)_{1-x}$, $(V_2O_5)_x(SiO_2)_{1-x}$, $(V_2O_5)_x(\gamma-Al_2O_3)_{1-x}$, $CuO_2$, $SnO_2$, NiO, $Fe_3O_4$, $Nb_2O_5$, lanthanum copper ferride, lanthanum strontium manganese copper ferride, $Cu_xMo_6S_8$, and mixtures thereof, wherein x is 0.01 to 0.99, and the other layer is an electron conducting layer; and
(d) a circuit that applies a potential across said anode and either said porous oxide catalyst or said electron conducting layer.

12. The electrochemical cell of claim 11 wherein said electron conducting layer is sandwiched between the solid electrolyte and the porous catalyst, and serves as a cathode.

13. The electrochemical cell of claim 11 wherein said porous catalyst is sandwiched between the solid electrolyte and the electron conducting layer, and serves as a cathode.

* * * * *

UNITED STATES PATENT AND TRADEMARK OFFICE
CERTIFICATE OF CORRECTION

PATENT NO. : 5,401,372
DATED : March 28, 1995
INVENTOR(S) : Liu et al.

It is certified that error appears in the above-indentified patent and that said Letters Patent is hereby corrected as shown below:

In column 3, line 30, in the equation, change "½O⁻" to --½O⁼--;

In column 3, line 46, in the equation, change "2e" to --2e⁻--;

In column 3, line 50, insert several spaces between "½O$_2$" and "X=1,2";

In column 4, line 5, change "($\gamma$-Al$_2$O$_2$)$_{1-x}$" to --($\gamma$-Al$_2$O$_3$)$_{1-x}$--;

In column 4, line 7, in second equation, change "Co$_{1-x}$Fe$_x$" to --Co$_{1-z}$Fe$_z$--;

In column 4, line 8, in the first equation, after "Cu$_y$" delete "," and change "Fe$_x$" to --Fe$_z$--;

In column 4, line 18, change "(Bi$_2$O$_2$)" to --(Bi$_2$O$_3$)--;

In column 4, line 42, delete one of the "Co$_y$";

In column 5, line 43, after "NH$_4$" delete ",";

In column 6, line 13, change "500" to --550--;

In column 6, line 36, after "The Phases of the powder" change "was" to --were--;

In column 6, line 54, change "ZrO$_2$pellets" to --ZrO$_2$ pellets--;

In column 7, line 55, change "Results" to --results--;

UNITED STATES PATENT AND TRADEMARK OFFICE
CERTIFICATE OF CORRECTION

PATENT NO. : 5,401,372
DATED : March 28, 1995
INVENTOR(S) : Liu et al.

It is certified that error appears in the above-indentified patent and that said Letters Patent is hereby corrected as shown below:

In column 8, line 2, change "region" to --reduction--;

In column 8, line 53, after "min." change "-" to -- = --;

In column 9, line 12, after "surface" delete "a";

In column 9, line 21, change "No$_x$" to --NO$_x$--;

In column 9, line 30, change "4.5) to --(4.5)--;

In column 9, line 49, after "output" change the period to a comma.

Signed and Sealed this

Seventeenth Day of September, 1996

Attest:

BRUCE LEHMAN

Attesting Officer

Commissioner of Patents and Trademarks